(12) United States Patent  
Savarino (10) Patent No.: US 7,553,844 B2  
(45) Date of Patent: Jun. 30, 2009

(54) METHODS FOR TREATMENT OF HIV OR MALARIA USING COMBINATIONS OF CHLOROQUINE AND PROTEASE INHIBITORS

(75) Inventor: Andrea Savarino, Vinovo (IT)

(73) Assignee: Jarrow Formulas, Inc., Los Angeles, CA (US)

( * ) Notice: Subject to any disclaimer, the term of this patent is extended or adjusted under 35 U.S.C. 154(b) by 706 days.

(21) Appl. No.: 10/783,268

(22) Filed: Feb. 20, 2004

(65) Prior Publication Data

US 2005/0009810 A1     Jan. 13, 2005

Related U.S. Application Data

(60) Provisional application No. 60/471,038, filed on May 16, 2003, provisional application No. 60/449,517, filed on Feb. 21, 2003.

(51) Int. Cl.  
    *A61K 31/00*      (2006.01)  
    *A61K 9/14*      (2006.01)

(52) U.S. Cl. .................. 514/299; 424/489; 424/490; 424/494; 424/455

(58) Field of Classification Search .............. 424/484, 424/489, 494, 455; 514/292, 248, 312, 1, 514/675  
See application file for complete search history.

(56) References Cited

U.S. PATENT DOCUMENTS

| | | | |
|---|---|---|---|
| 5,278,173 A * | 1/1994 | Davis .................... | 514/312 |
| 5,668,149 A | 9/1997 | Oroszlan et al. | |
| 6,221,400 B1 * | 4/2001 | Liversidge et al. ......... | 424/489 |
| 6,265,406 B1 * | 7/2001 | Patel et al. ............... | 514/248 |
| 2002/0071863 A1 * | 6/2002 | Dong et al. ............... | 424/455 |
| 2002/0077271 A1 * | 6/2002 | Cerami et al. ............. | 514/1 |
| 2002/0177603 A1 * | 11/2002 | Johnson et al. ........... | 514/292 |
| 2004/0102431 A1 | 5/2004 | Boss | |

FOREIGN PATENT DOCUMENTS

| | | |
|---|---|---|
| EP | 1 374 867 | 1/2004 |
| WO | WO/92/00145 | 2/1992 |
| WO | WO 97/08180 | 3/1997 |

OTHER PUBLICATIONS

Andrey Semenov, Jed E. Olson and Philip J. Rosenthal, Antimalarial Synergy of Cysteine and Aspartic Protease Inhibitors, Antimicrobial Agents and Chemotherapy, vol. 42(9), 2254-2258, 1998.*

Johan R. Boelaert, Kirk Sperber and Jacquew Piette, The additive in vitro anti-HIV-1 effect of chloroquine, when combined with zidovudine and hydroxyurea, Biochemical pharmaccology, 61, 1531-1535, 2001.*

Savarino, A. t al., The anti-HIV-1 activity of chloroquine. *Journal of Clinical Virology*, 20:131-135 (2001). Elsevier Science.

Savarino, A., et al., Anti-HIV effects of chloroquine: mechanisms of inhibition and spectrum of activity. *Aids*, 15:2221-2229 (2001). Lippincott Williams & Wilkins.

Savarino, A., et al., Anti-HIV Effects of Chloroquine. *Journal of Acquired Immune Deficiency Syndrome*, 35(3):223-232 (2004). Lippincott Williams & Wilkins.

Sidhu, A., et al., Chloroquine Resistance in *Plasmodium falciparum* Malaria Parasites Conferred by pfcrt Mutations. *Science*, Oct. 4, 298:210-213 (2002).

Savarino, A., et al., Human CD38 interferes with HIV-1 fusion through a sequence homologous to the V3 loop of the viral envelope glycoprotein gp120. *FASEB*, Jan. 22, 10.1096/fj.02-0512fje. (2003).

Mammano, F., et al., Retracing the Evolutionary Pathways of Human Immunodeficiency Virus Type I Resistance to Protease Inhibitors: Virus Fitness in the Absence and in the Presence of Drug. *Journal of Virology*, 74(18): 8524-8531 (2000).

Nathoo, S., et al., Effect of HIV-1 antiretroviral drugs on cytoadherence and phagocytic clearance of *Plasmodium facliparum*-parasitised erythrocytes. *The Lancet*, Sep. 27, 362:1039-1041 (2003).

Ward, SA. Bray, PG., Definitive proof for a role of pfmdr 1 in quinoline reistance in *Plasmodium falciparum*. *Drug Resistance Updates*, April, 3(2): 80-81 (2000).

Makler, MT, et al., Parasite lactate dehydrogenase as an assay for *Plasmodium falciparum* drug sensitivity. *Am J Trop Med Hyg.*, Jun. 48(6):739-741 (1993).

"No drug-drug interaction between nelfinavir or indinavir and mefloquine in HIV-1-infected patients." AIDS (London, England) Dec. 1, 2000 vol. 14, No. 17, Schippers, E. F., et al.

"Pharmacokinetic interaction between mefloquine and ritonavir in healthy volunteers." British Journal of Clincial Pharmacology, Jun. 2001, Khaliq, U., et al.

"Hydroxychloroquine, hydroxycarbamide, and didanosine as economic treatment for HIV-1." Lancet. May 11, 2002, vol. 359, No. 9318, Paton, Nicholas I., et al.

"Comparison of hydroxychloroquine with zidovudine in asymptomatic patients infected with human immunodeficiency virus type 1." Clinical Therapeutics, Sep.-Oct. 1997 vol. 19, No. 5, Sperber, K., et al.

Clin. Ther., Sep. 1999, vol. 21, p. 1456-1496, Okereke.

Treatment for HIV related inflammation, Treatment Review, May 1995 (No. 18) Abstract.

Hydroxychloroquie=ddl=hydroxyurea antiretroviral trial, AIDS Research Alliance, Los Angeles, AIDS Treatment News, Dec. 3, 1990 (No. 332).

Boelaet, et al. The Additive I Vitro and Anti-HIV-1 Effect of Chloroquine, When Combined with Zidovudine and Hydroxyurea, Biochemical Pharmacology, 2001, vol. 61, pp. 1531-1535.

Chukwuemeka, A Management of HIV-Infected Pregnant Patients in Malaria-Endemic Areas; Therapeutic and Safety Considerations in ConComitant Use of Antiviral and Antimalarial Agents, Clinic Therapeutics, 1999, vol. 21, No. 9, 1999, pp. 1456-1496.

\* cited by examiner

*Primary Examiner*—Michael G Hartley  
*Assistant Examiner*—Jagadishwar R Samala  
(74) *Attorney, Agent, or Firm*—McCarter & English, LLP (57) ABSTRACT

The present invention relates to a drug combination capable of conferring therapeutic benefits in the treatment of both AIDS and malaria. In particular, it relates to a drug combination including at least one quinolinic antimalarial compound such as chloroquine or hydroxychloroquine, and at least one inhibitor of the Human Immunodeficiency Virus (HIV) protease enzyme. This drug combination is capable of inhibiting the replication of both HIV and *Plasmodium* sp. It also relates to the direct antimalarial effects of the HIV PIs.

2 Claims, 7 Drawing Sheets

Figure 1, View 1

Figure 1, View 2

Figure 2

```
              10        20        30        40        50        60
              ....*....|....*....|....*....|....*....|....*....|....*....|
P. falc   1   lqssndnielvdfqNIMFYGDAEVGnQQPFTFILDTGSANLWVPSVkcttagcltkhly  60
HIV 1pr   1   ~~~~~~~~pqitlWQRPVVTIKIG--GQLMEALIDTGADDTVLEEMll~~~~~~~~~~~~~  38

70        80        90       100       110       120
              ....*....|....*....|....*....|....*....|....*....|....*....|
P. falc   61  dssksrtyeKDGTKVEMNYVSgtvSGFFSKDLVTVGNLSLPYKFIEVLdtngfeptyta  119
HIV 1pr   39  ~~~~~~~~pGRWKPKIIGGIGfvKVRQYDQPIEICGHKVIGTVLVGPt~~~~~~~~~~  80

130       140       150       160       170       180
              ....*....|....*....|....*....|....*....|....*....|....*....|
P. falc   120 stfDGILGLgwkdlsigsvdpivvelknqnkienalftfylpvhdkhtgfltiggieerf  179
HIV 1pr   81  ~pTNIIGRnlltqigctlnf~~~~~~~~~~~~~~~~~~~~~~~~~~~~~~~~~~~~~~~  99

190       200       210       220       230       240
              ....*....|....*....|....*....|....*....|....*....|....*....|
P. falc   180 yegpltyeklnhdlywqitldahvgnimlekancivdsgtsaitvptdflnkmlqnldvi  239
HIV 1pr       ~~~~~~~~~~~~~~~~~~~~~~~~~~~~~~~~~~~~~~~~~~~~~~~~~~~~~~~~~~~

250       260       270       280       290       300
              ....*....|....*....|....*....|....*....|....*....|....*....|
P. falc   240 fyvtlcnnsklptfeftsengkytlepeyylqhiedvgpglcmlniigldfpvptfilgd  299
HIV 1pr       ~~~~~~~~~~~~~~~~~~~~~~~~~~~~~~~~~~~~~~~~~~~~~~~~~~~~~~~~~~~

310       320
              ....*....|....*....|....*.
P. falc   300 pfmrkyftvfdydnhsvgialakknl  325
HIV 1pr       ~~~~~~~~~~~~~~~~~~~~~~~~~~
```

METHODS FOR TREATMENT OF HIV OR MALARIA USING COMBINATIONS OF CHLOROQUINE AND PROTEASE INHIBITORS

This application claims priority to provisional patent application Ser. No. 60/449,517 filed on Feb. 21, 2003 and provisional patent application Ser. No. 60/471,038 filed on May 16, 2003, the contents of both of which are incorporated herein in their entirety.

In addition, the following Sequence Listing material is contained on a disc, and the files are hereby incorporated-by-reference into the present application in their entirety: Savarino Sequence Listing, Patent In Document, 2 KB, created Sep. 21, 2004; Savarino Sequence Listing, Microsoft Word Document, 41 KB, created Sep. 21, 2004; Savarino Sequence Listing, Text Document, 6 KB, created Sep. 21, 2004. Print copies of the Sequence Listings are included as an Appendix to the current Application, and are also incorporated-by-reference herein in their entirety.

FIELD OF THE INVENTION

The present invention relates to a drug combination capable of conferring therapeutic benefits in the treatment of both acquired immunodeficiency syndrome (AIDS) and malaria. In particular, it relates to a drug combination comprising chloroquine or hydroxychloroquine plus an inhibitor of the HIV protease capable of inhibiting the replication of both the human immunodeficiency viruses (HIV) and *Plasmodium* sp. The present invention also relates to the direct antimalarial effects of the HIV protease inhibitors.

BACKGROUND OF THE INVENTION

Acquired immunodeficiency syndrome (AIDS) and malaria are among the most devastating infectious diseases that have ever affected mankind, causing approximately five million deaths per year in the world. The effects of these diseases are most pronounced in underdeveloped countries in that the diseases are accompanied by financial and living conditions that are already miserable to start with. Several resource-poor countries cannot afford effective therapies that might allow the prevention of many deaths. The difficulties per se in treating both AIDS and malaria, caused in part by the drug-resistance of both their etiological agents, i.e., the human immunodeficiency viruses (HIV) and protozoa belonging to the genus *Plasmodium,* become exaggerated when the pharmaceutical weapons are extremely limited. In several resource-poor countries with high rates of HIV seroprevalence, the use of highly active antiretroviral therapy (HAART) has encountered major obstacles due to its high costs and the complexities of its prescription. Recently, due to humanitarian considerations, anti-HIV drugs have been offered at reduced prices to some of the least developed countries with a high HIV seroprevalence. The problem is, however, still far from being solved. Compared to antiretrovirals, antimalarials have lower costs, which may in any case weigh heavily on the budgets of several poorer countries. Chloroquine (CQ), recommended for a long time by the World Health Organization (WHO) as a first line treatment of malaria, is still the most affordable and widely adopted antimalarial option in Africa; however, the continuous emergence of drug-resistant *Plasmodium* strains renders its administration ineffective in a large number of areas in Africa, Latin America and South-Eastern Asia.

As most of the areas heavily stricken by AIDS also exhibit endemic malaria (and frequently individuals are co-infected), it would be useful to develop a treatment effective against both diseases.

In this regard, CQ may be particularly useful in that it has been demonstrated to exhibit in-vitro activity against HIV-1 replication and against several AIDS-related opportunistic microorganisms. It also has well-documented, long-term safety when used in immunocompromised individuals, (including those with HIV/AIDS), when dosed for antimalarial prophylaxis and in the treatment of rheumatic diseases. Although no information is available on the in-vivo effects of CQ on viral load, its hydroxy-analog hydroxychloroquine (HCQ) has proven in-vivo anti-HIV-1 activity. The anti-HIV activity of CQ is due to an impairment of the infectivity of virions produced by cells treated with the drug. Although the present invention is not limited to any particular mechanism, it is believed that the mechanism behind this inhibitory effect is inhibition of gp120 glycosylation. This hypothesis is supported by results showing that CQ impairs the formation of the heavily glycosylated epitope 2G12, which is located on the gp120 envelope glycoprotein surface and is fundamental for virus infectivity. These effects show that CQ inhibits viral replication by a mechanism different than those of currently used antiretroviral drugs, and this new mechanism has led to testing CQ in combination with antiretrovirals in clinical trials.

More detailed information on the anti-HIV effects of CQ can be found in the following two articles, which are hereby incorporated in the present patent application in their entirety:

Savarino A, Gennero L, Chen H C, Serrano D, Malavasi F, Boelaert J R, Sperber K. Anti-HIV effects of chloroquine: mechanisms of inhibition and spectrum of activity. AIDS Nov. 23, 2001; 15(17):2221-9.

Savarino A, Gennero L, Sperber K, Boelaert J R. The anti-HIV-1 activity of chloroquine. J Clin Virol 2001 February; 20(3):131-5.

It is known that CQ may exert additive effects when associated with other anti-HIV drugs such as ddI, hydroxyurea, and AZT. The effects of a combinatorial administration of CQ and inhibitors (PIs) of the HIV protease (SEQ ID NO: 1) have however been totally unknown until the present invention. In view of the future large-scale administration of PI-based regimens in malaria-endemic areas, this interaction may provide the following: 1) CQ/HCQ and PIs are the only drugs tested in humans that inhibit HIV replication at a post-integrational stage; 2) the effects of both CQ and PIs result in an impairment of the infectivity of newly produced virions; 3) both CQ and PIs are substrates of and, at varying levels, inhibit important cell surface drug transporters, ie., the P-glycoprotein (P-gp) and the multi-drug resistance-associated proteins (MRP), which belong to the ATP-binding cassette family and modulate the intracellular concentrations of antiretroviral drugs. Of note, recent data indicate that CQ is capable of increasing the level of inhibition of P-gp- and MRP-mediated efflux exerted by PIs in CD4$^+$ lymphocytes (Savarino et al., JAIDS 2004, in press).

The inhibitory effects of PIs on cell surface drug transporters may make the combination of CQ and a PI particularly useful in treatment of malaria.

Drug transport on the cell surface has been hypothesized to be involved in plasmodial drug-resistance. This theory is supported by several pieces of evidence.

First, a glycoprotein of *P. falciparum,* namely Pf-MDR, presents a high degree of homology with human P-gp and may be in some ways related to CQ-resistance. Ward S A, Bray P G. Definitive proof for a role of pfmdr 1 in quinoline resistance in *Plasmodium falciparum*. Drug Resist Updat 2000 April;3(2):80-81

Second, CQ-resistance in vitro is characteristically reverted by verapamil, a known inhibitor of the ATP-binding cassette in human cells. Sidhu A B, Verdier-Pinard D, Fidock D A. Chloroquine resistance in *Plasmodium falciparum* malaria parasites conferred by pfcrt mutations. Science Oct. 4, 2002;298(5591):210-3

Third, erythrocytes parasited by CQ-resistant *P. falciparum* strains accumulate more limited intracellular CQ pools than those parasited by CQ-sensitive strains. The capacity of a *P. falciparum* strain to decrease CQ accumulation within erythrocytes is strictly associated with mutations in a gene (Pf-crt) that encodes the so-called CQ-resistance transport (CRT) protein. The precise mechanisms by which *P. falciparum* CRT intervenes in these phenomena have not been elucidated yet. Of note, these mutations are present in the vast majority of the CQ-resistant field isolates of *P. falciparum* coming from different areas of the world and are not present in CQ-sensitive isolates. Sidhu A B, Verdier-Pinard D, Fidock D A. Chloroquine resistance in *Plasmodium falciparum* malaria parasites conferred by pfcrt mutations. Science Oct. 4, 2002;298(5591):210-3.

It would be beneficial to have compositions and treatments using a combination of CQ and a PI that inhibits both HIV and *Plasmodium* sp.

SUMMARY OF THE INVENTION

The present invention relates to a drug combination capable of conferring therapeutic benefits in the treatment of both AIDS and malaria. In particular, it relates to a drug combination including an inhibitor of the HIV protease (SEQ ID NO: 1) plus CQ or HCQ or another antimalarial with similar characteristics. This drug combination is capable of inhibiting the replication of both HIV and *Plasmodium* sp. It also relates to the direct antimalarial effects of the HIV PIs.

The combination claimed in the present patent application unexpectedly demonstrated enhanced capability of conferring a more sustained inhibition of both HIV and *Plasmodium* sp. than the single agents administered alone, that is, CQ can reinforce the antiretroviral activity of a PI and a PI can strengthen the antimalarial activity of CQ.

The combination of a PI plus CQ may thus be used for the purpose of inhibiting HIV replication, for the purpose of inhibiting *Plasmodium* sp. growth, or for the purpose of inhibiting both agents.

From a clinical perspective, the combination of a PI plus CQ/HCQ may be capable of treating AIDS and malaria. Therefore, it can be utilized in the treatment of individuals infected with HIV, in individuals affected by or at risk for contracting malaria or in people with HIV/malaria coinfection.

Also, the combination of CQ and PIs can be used to restore the sensitivity of drug-resistant isolates of HIV and *P. falciparum* to the PIs and to CQ, respectively.

In another embodiment, the present invention relates to the intrinsic antimalarial effects of PIs. The present inventor found that PIs clinically used in the treatment of HIV exert direct antimalarial effects. These direct effects are observable in vitro at therapeutically achievable concentrations (See example III).

Although this invention is not related to any particular mechanism, bioinformatic analysis suggests that the target of PIs may be plasmepsin II (SEQ ID NO: 2), a member of the plasmepsins family, a potential target for new antimalarials.

DETAILED DESCRIPTION OF THE FIGURES

FIGS. 1 and 2 show the three-dimension structural superimposition and the corresponding sequence alignment between *P. falciparum* plasmepsin II (SEQ ID NO: 2), and the HIV-1 protease (SEQ ID NO: 1) obtained using the VAST algorithm (available in the NCBI website, http://www.ncbi.nlm.nih.gov). The three dimensional structure of plasmepsin II is available in the Protein Database (PDB; http://rcsb.org/pdb/). The HIV-1 protease shown is one of the many retroviral protease sequences retrieved by submitting the plasmepsin II structure to the NCBI database in search for structural neighbors. It is therefore shown just as an example and is not intended in any way to limit the scope of the invention.

FIG. 1 shows two different views of a superimposition of the three-dimension structures of the aligned domains of *P. falciparum* plasmepsin II and the HIV-1 protease. The residues significantly aligned and corresponding to the catalytic site of both molecules are represented by the dotted markings (. . . ). Regions of plasmepsin II with a lower level of alignment are represented by the crossed-line markings (xxxx). Similar regions of the HIV-1 protease are represented by the dashed-line markings (- - -). The molecular structure of the PI indinavir (IDV) in complex with the HWI-1 protease is also shown as the darkly shaded regions.

FIG. 2 shows the sequence alignment corresponding to the three-dimensional alignment shown in FIG. 1. The markings that appear above or below the residues strictly correspond to those of FIG. 1 and are described in the previous paragraph. Regions shown without any corresponding markings correspond to the unaligned domains (not shown in FIG. 1).

FIG. 3 shows the combined effects of CQ and HIV PIs on viral replication. Briefly, MT-4 cells or primary peripheral blood mononuclear cells (PBMC) were inoculated with laboratory strains or primary isolates, respectively. The HIV-infected cells were then incubated with selected concentrations of IDV and/or CQ.

FIG. 3A shows the effects of CQ on HIV-1 IIIB replication in MT-4 cells in the presence of IDV. The decrease in production of HIV-1 p24 in the presence of CQ+IDV is shown (means ±S.E.M.; 3 experiments). In this case, cells were infected with a low multiplicity of infection (0.01), in order to better unmask any favoring effects of the IDV/CQ combination on HIV-1 replication.

FIG. 3B is an isobologram demonstrating the fractional inhibitory concentrations of the combination CQ+IDV against HIV-1 IIIB replication. The fractional inhibitory concentrations (FIC) of the CQ+PI combination capable of inhibiting viral replication by 90% ($EC_{90}$) are shown. The curve best fitting the data points was calculated according to a non-linear regression model. The graph shows the expected line in case of simply additive effects (connecting the 1.0 FIC values on the x and y axes) as well as the threshold between sub-synergistic and truly synergistic effects (ie., the line connecting the 0.5 FIC values).

FIG. 3C shows isoboles demonstrating the fractional inhibitory concentrations of the combinations CQ+saquinavir (SQV) and CQ+ritonavir (RTV) against HIV-1 IIIB replication. As in the preceding panel, this graph shows the FIC of the CQ+PI resulting in the $EC_{90}$. The lines and curves presented were obtained as described in the previous paragraph.

FIG. 3D shows the enhanced response to IDV of a primary isolate (VI829, HIV-1 Clade C) in the presence or absence of CQ. In this panel, and in the following ones, viral replication is presented as the percentage of untreated controls so as to allow an easy comparison between the effects of IDV in the presence or absence of CQ (1 μM). Differences between CQ-treated and untreated cultures are evident from the regression lines best matching the data points and resulting in a difference of approximately 1 Log in the $EC_{50}$ of IDV (marked in the graph).

FIG. 6A. Effects of RTV (50 mg/kg) on *P. berghei* growth in Balb/c mice. Results are shown as an average ±S.D. of the percentage of parasitized red blood cells at different days of follow-up.

FIG. 6B. Effects of RTV (50 mg/kg) on survival of mice infected with *P. berghei*. Results are shown as Kaplan Meyer curves and the P value for difference in survival is reported.

FIG. 6C. Effects of RTV (150 mg/kg) on *P. berghei* growth in Balb/c mice. Results are shown as an average ±S.D. of the percentage of parasitized red blood cells at different days of follow-up.

FIG. 6D. Effects of RTV (150 mg/kg) on survival of mice infected with *P. berghei*. Results are shown as Kaplan Meyer curves and the P value for difference in survival is reported.

DETAILED DESCRIPTION OF THE INVENTION

The present invention relates to a drug combination effective against both of the etiological agents of the two major infectious diseases in the world, ie., AIDS and malaria. In particular, it relates to a drug combination including an inhibitor of the HIV protease (SEQ ID NO: 1) plus an antimalarial such as, for example, CQ or HCQ, capable of inhibiting the replication of both HIV and *Plasmodium* sp.

The combination claimed in the present patent application may be capable of conferring a more sustained inhibition of both HIV and *Plasmodium* sp. than the single agents alone, that is, CQ can reinforce the antiretroviral activity of a PI and a PI can strengthen the antimalarial activity of CQ.

As the therapeutic benefit of the above-described combination can be seen on both HIV and *Plasmodium* sp., the combination may be used for the purpose of inhibiting HIV replication, for the purpose of inhibiting *Plasmodium* sp. growth, or for the purpose of inhibiting both HIV replication and *Plasmodium* sp. growth.

From a clinical perspective, the combination of a PI plus an antimalarial such as CQ/HCQ can be used for treatment of AIDS and malaria. Therefore, it could be utilized in the treatment of individuals infected with HIV, in individuals affected by or at risk for contracting malaria or in people with HIV/malaria coinfection. The two agents used in combination may increase the inhibition level of drug-sensitive HIV and *Plasmodium* strains, but also that the combination PI+CQ restores the sensitivity of drug-resistant isolates of HIV and *P. falciparum* to the PIs and to CQ, respectively.

Regarding the treatment of HIV, it is important to point out that the effects of CQ in combination with protease inhibitors are synergistic. When administered to acutely infected cells in combination with a PI, CQ decreases the concentration of PIs necessary to produce a certain level of HIV inhibition [see EXAMPLE 1].

In addition, CQ partially restores sensitivity to PIs in PI-resistant strains, as exemplified below [see EXAMPLE 1].

Although the invention is not limited to any particular mechanism, it is believed that the use of a P-gp and MRP blocking agent such as CQ may increase the intracellular concentrations of PIs.

In one embodiment, the present invention allows a treatment strategy whereby the co-administration of an antimalarial, such as CQ/HCQ or another quinolinic agent, to HIV positive individuals allows the effective dose of PIs to be decreased, lessening cost and possibly toxicity. Also, the ability of CQ to overcome resistance to PIs could be of greatest importance for the treatment of drug-experienced HIV positive subjects who have developed multiple resistance to antiretroviral drugs and thus have limited therapeutic options.

Embodiments of the present invention may also be used in the treatment of drug-resistant malaria. Indeed, in several areas of the world with endemic malaria, *P. falciparum* strains with a multi-drug resistant phenotype are becoming prevalent, and the use of a PI may restore sensitivity to CQ. The availability of one such drug may therefore be expected to save enormous numbers of lives. Cost-related problems in Third World areas where PIs are currently not affordable are expected to be resolved—at least partially—in the near future when PIs will become available on a large scale for the treatment of HIV infection. Considering that AIDS and malaria often co-exist in the same areas, PIs may become more commonly available in those areas than they are today, and therefore it will be possible to postulate a more cost effective use of these drugs in the treatment of malaria. Similarly, HIV-infected individuals living in areas with endemic drug-resistant malaria and treated with the PI+CQ combination may become protected from the occurrence of malarial episodes.

Furthermore, said effects of PIs in combination with a quinolinic agent may contribute to a revival of drugs such as CQ and first generation PIs (RTV, SVQ, IDV), which otherwise would be doomed to be replaced by newer drugs in the near future.

To sum up, the present invention involves administration of a drug combination that may be effective against HIV and malaria. Embodiments of the combination may include:
1) chloroquine (CQ) or hydroxychloroquine (HCQ) or another quinolinic agent such as mefloquine (MQ) and quinine (Q) combined with
2) one or more inhibitors of the HIV protease (PIs).

PIs may Include:

Indinavir (IDV), ritonavir (RTV), saquinavir (SQV), nelfinavir (NFV), lopinavir (LPV), the combination RTV plus LPV, amprenavir (APV), fosamprenavir (FPV), tipranavir (TPV), atazanavir (ATZ), TMC-114.

The antimalarial and PI combination may be administered with the contemporary co-administration of nucleosidic inhibitors of the HIV reverse transcriptase (NRTIs).

NRTIs may Include:

Zidovudine (AZT or ZDV), lamivudine (3TC), abacavir (ABC), zalcitabine (ddC), didanosine (ddI), stavudine (d4T), tenofovir (TDF), emitricitabine (FTC), amdoxovir (DAPD).

The invention is not limited in this regard, and any appropriate quinolinic agent, PI and/or NRTI may be used.

The antimalarial and PI combination may also be administered with the contemporary co-administration of other antimalarial drugs, or with the contemporary co-administration of antibiotics against concomitant infections, or any drug against co-existing or related diseases.

The present invention also relates to the direct antimalarial effects of the HIV PIs. Not only can PIs revert CQ resistance, but PIs also are endowed with intrinsic antimalarial effects. These direct effects are observable in vitro at therapeutically achievable concentrations (See example II) and in vivo in a murine malaria model (See example III).

Figure 1:
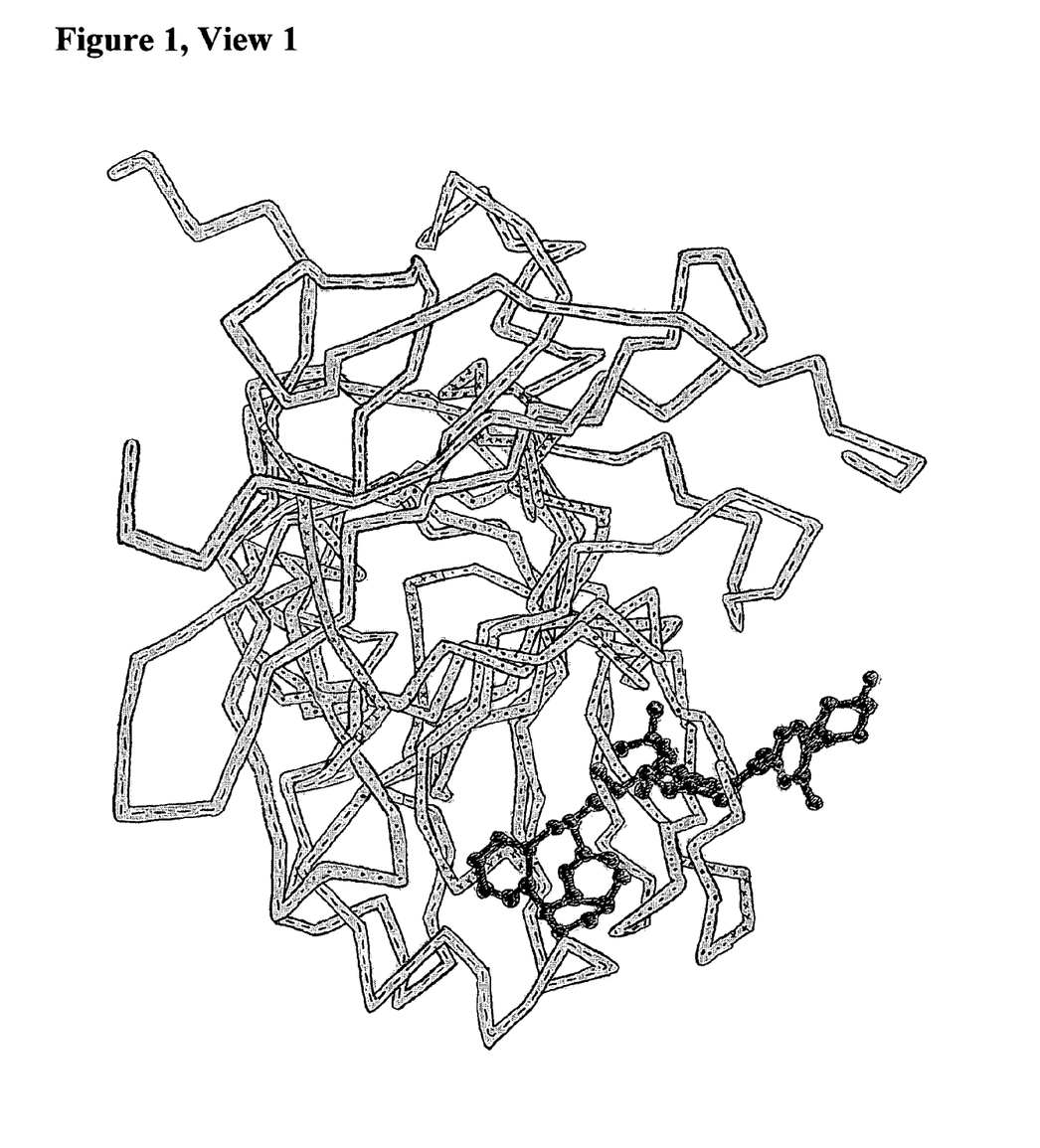
Figure 2:
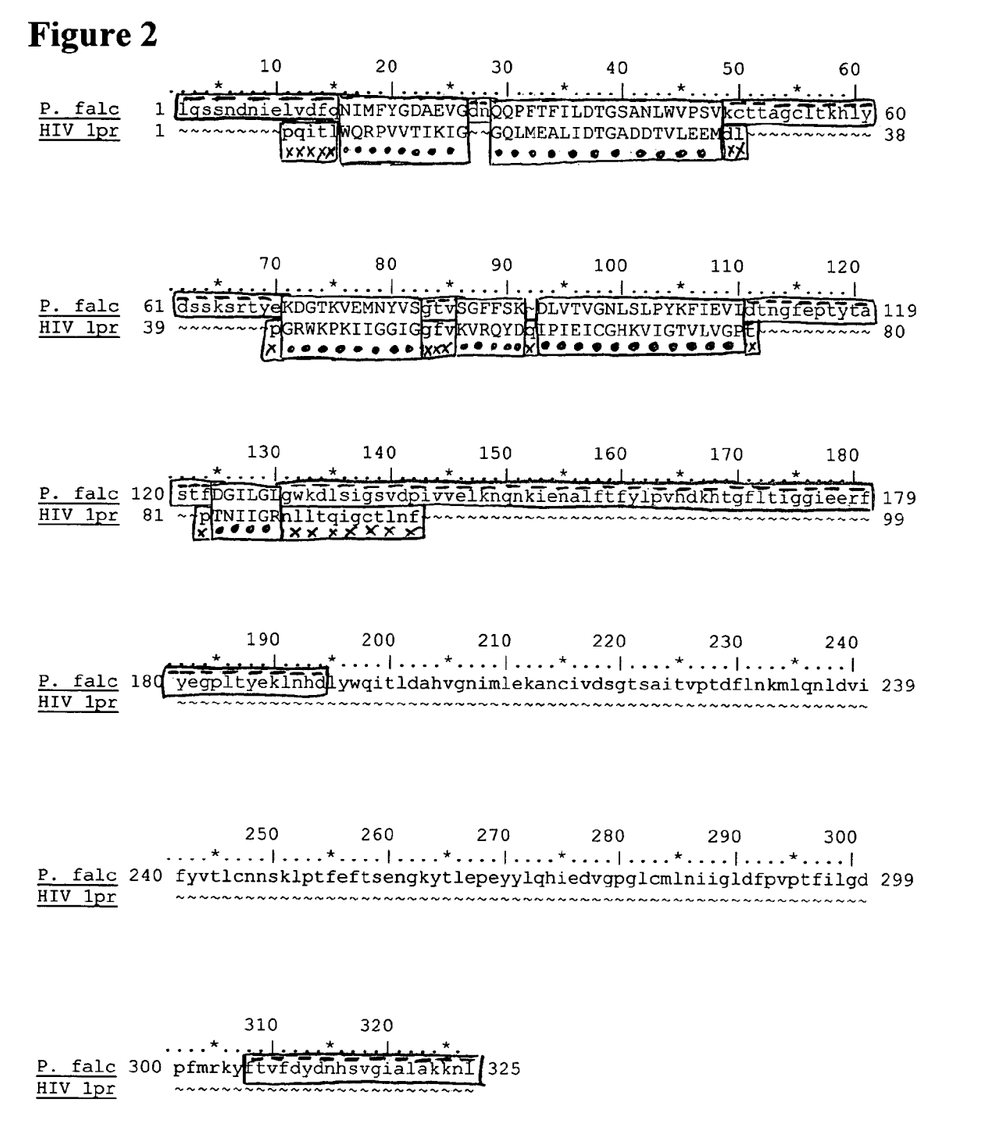

The mechanism for the direct antimalarial effects of PIs has not been elucidated yet. Interesting insights however come from the observation that the HIV-1 protease (i.e., the target against which these drugs were designed) shares a significant sequence- and structure-similarity with proteases which are members of the plasmepsins family of *Plasmodium* sp.(FIGS. 1 and 2; SEQ ID NO: 1 AND 2). Similarly to the HIV-1 protease, plasmepsins are aspartyl-proteases and have a fundamental role in the intracellular growth of *P. falciparum*. They intervene in the first steps of the degradation of hemoglobin, which constitutes the principal nutrient for the intraerythrocytic stages of the parasite. Given the structural similarity between the HIV-1 protease and plasmepsins, it is possible to hypothesize that PIs impair plasmodial growth by targeting these enzymes. This hypothesis is sustained by the fact that the regions of maximal similarity between the two proteins is their catalytic site, which, in the HIV-1 protease, is non-covalently bound to and inhibited by PIs. If this mechanism is confirmed by experimental data, the HIV PIs will become the first drugs subjected to safety tests in humans to inhibit a member of the plasmepsins family, recently indicated by WHO as a potential target for the development of new antimalarials. In a time in which drug-resistant *Plasmodium* strains are continuously emerging, the availability in the pharmaceutical arsenal of drugs directed to a new target will increase the therapeutic options.

Other potential ground for the antimalarial effect of PIs is the recently described down-modulation of CD36 (a receptor for *P. falciparum*) induced by these drugs in human erythrocytes. Nathoo S, Serghides L, Kain K C. Effect of HIV-1 antiretroviral drugs on cytoadherence and phagocytic clearance of *Plasmodium falciparum*-parasitised erythrocytes. Lancet. Sep. 27, 2003;362(9389):1039-41.

The description of the mechanisms reported above has been done only for explanatory purposes: the present invention relates to the effects of PIs on *Plasmodium* sp. growth in vitro and in vivo and is not limited to any particular mechanism.

The direct antimalarial effects of PIs corroborate their use in combination with CQ, as described above. The direct antimalarial effect of PIs also indicates that HIV-infected individuals living in areas with endemic malaria and treated with an antiretroviral cocktail including a PI may become protected, at least partially, from the occurrence of malarial episodes. Protection from malarial episodes is an advantage for treatment of HIV in view of the limited budgets of several resource-poor countries. Indeed, in Sub-Saharan Africa, there are malaria-endemic areas where the levels of HIV seroprevalence can reach 30%. As HIV-infected people are at higher risk for complicated malaria, one can imagine that the direct anti-plasmodial effects of a PI could save a huge amount of human and financial resources.

The invention will now be further described by way of Examples, which are meant to serve to assist one of ordinary skill in the art in carrying out the invention and are not intended in any way to limit the scope of the invention.

EXAMPLES

Materials and Methods

Infection Assays

Laboratory-adapted HIV-1$_{IIIB}$ and HIV-2$_{CBL/20}$ strans, the primary isolates HIV-1$_{UG3}$ (Clade A, R5) and HIV-1$_{VI\ 829}$ (Clade C, R5), both obtained from antiretroviral-naive subjects were used. These viruses are fully described in the paper by Savarino A. et al. referenced above. The HIV-1$_{PAVIA12}$ isolate was also used. It was donated by Dr. Maurizia Debiaggi, University of Pavia, Italy, who also performed its genotypic analysis. It belongs to Clade B and was isolated from an individual with HAART failure. It possesses a genotypic profile of multi-drug resistance to all classes of antiretrovirals currently utilized in the medical practice (Mutations in the HIV-1 reverse transcriptase: 67N 69D 70R 74V 108I 181C 184V 219Q 228R; Mutations in the HIV-1 protease: 10I 20R 36I 46L 54V 55R 63P 71V 82A 90M). Viral stocks were titrated biologically by the 50% endpoint dilution method, using MT-2 cells (laboratory strains) or PHA-activated peripheral blood mononuclear cells (PBMC) (primary isolates).

In acute infection assays, the appropriate cell types were incubated at 37° C. for 2 h with the viral stock suspensions at a multiplicity of infection (MOI) of approximately 0.1, unless otherwise specified. After three washes, cells were incubated in fresh culture medium for 7 days at 37° C., and cell-free supernatants at different intervals post-infection were harvested for ELISA measurement of HIV-1 p24 (NEN Life Science Prod., Boston Mass.) or HIV-2 p27 (Coulter, Hialeah, Fla.) (26, 33). Cells were then incubated, after virus adsorption, in the presence of concentrations of CQ reachable in plasma of individuals under CQ treatment.

The selectivity index was calculated as the IC$_{50}$/EC$_{50}$ ratio. In the case of infection of PBMC, a toxicity curve was done for each donor so as to have a precise estimate of the selectivity index.

The CD4$^+$ CXCR4$^+$ MT-4 T-cell line was used to assess the effects of CQ and PIs on the X4 laboratory-adapted strains, whereas peripheral blood mononuclear cells (PBMC) obtained by informed consent from healthy donors and stimulated for three days with 2 μg/ml phytohemagglutinin (PHA; Difco Laboratories, Detroit, Mich.) were adopted in assays using primary isolates.

More detailed information on the virological procedures followed can be found in the article: Savarino A, Gennero L, Chen H C, Serrano D, Malavasi F, Boelaert J R, Sperber K. Anti-HIV effects of chloroquine: mechanisms of inhibition and spectrum of activity. AIDS Nov. 23, 2001;15(17):2221-9, which is incorporated herein by reference in its entirety.

Assays for Evaluation of Toxicity

In the uninfected controls, cell viability and apoptosis were analyzed by trypan-blue exclusion, by the MTT method and by propidium iodide/annexin V FITC staining as determined by techniques previously validated by the present inventor. More detailed information on the virological procedures followed can be found in the article: Andrea Savarino, Thea Bensi, Annalisa Chiocchetti, Flavia Bottarel, Riccardo Mesturini, Enza Ferrero, Liliana Calosso, Silvia Deaglio, Erika Ortolan, Stefano Buttò, Aurelio Cafaro, Toshiaki Katada, Barbara Ensoli, Fabio Malavasi, and Umberto Dianzani (2003) Human CD38 interferes with HIV-1 fusion through a sequence homologous to the V3 loop of the viral envelope glycoprotein gp120. The FASEB Journal Express Article 10.1096/fj.02-0512fje, which is incorporated herein by reference in its entirety.

Assessment of Synergism

To measure synergism, cell pellets were resuspended in media containing different combinations of CQ and IDV after viral adsorption onto cells. A fractional inhibitory concentration (FIC) was then calculated as drug $EC_{90}$ of drug A in combination with drug 2/$EC_{90}$ of drug B alone. The effect was considered to be synergistic when the sum of FICs was $\leq 0.5$.

Parasites

Ibginovia is an isolate obtained at the Istituto Superiore di Sanità, Rome, Italy, positive for mutations in the codons K76 and A220 of the pfcrt gene conferring CQ resistance. The parasite's origin is Nigeria. All parasites were maintained in vitro in RPMI 1640 medium to which was added human type A red blood cells (RBC) and 10% heat-inactivated human serum. All cultures were placed in a humidified incubator at 37° C. with a gas-controlled environment of 3% $O_2$, 6% $CO_2$, and 91% $N_2$ and fed according to established procedures.

Detection of Parasitemia

Parasitemia was determined by light microscopy using Giemsa-stained thin smears and with fluorescence microscopy using the dye benzothiocarboxypurine.

Parasite Lactate Dehydrogenase Measurements

This assay is based on the principle that plasmodial lactate dehydrogenase (LDH) can use 3-acetylpyridine NAD (APAD) as a coenzyme, which is converted to APADH during lactate oxidation. All samples for LDH determination were measured spectrophotometrically at 650 nm. For these measurements, 10-50 μl of the malaria sample was added to the Mastat reagent, which is an optimized formulation for parasite LDH detection. The samples consisted of malaria cultures. All aliquots were added to 0.2 ml of the Malstat reagent using a 96-well microtiter plate format. The formation of APADH was determined at 650 nm using a multiwavelength plate reader. Each well of a test microtiter plate was automatically measured at 30-sec. intervals, and the individual data points were stored and subsequently plotted with a software program. The spectrophotometric assessment of LDH activity was facilitated by adding NBT (0.24 mM) and PES (0.033 mM) to Malstat reagent. As APADH is formed, the NBT is reduced and forms a formazan product that is blue and can be detected visually and measured at 650 nm. This assay is specific for parasitic LDH and is not influenced by the human enzyme. Makler M T and Hinrichs D J (1993) Measurement of lactate dehydrogenase activity of *Plasmodium falciparum* as an assessment of parasitemia. Am J Trop Med Hyg 48: 205-10

Example I

The purpose of this test was to analyze whether the addition of CQ to IDV might produce a level of HIV inhibition higher than that produced by IDV alone. HIV-1 IIIB-infected MT-4 cells were incubated in a medium containing 10 nM IDV in the presence or absence of increasing concentrations of CQ (1-6.25 μM). The IDV concentration chosen is close to the $EC_{50}$ in HIV-1 IIIB-infected MT-4 cells, as determined under our experimental conditions (data not shown). Addition of CQ did not result in significant differences in cell viability, thus excluding that the differences observed are due to a specific impairment of cell viability exerted by CQ (data not shown). The levels of p24 at 5 days post-infection in supernatants of cultures treated with CQ+IDV were lower than those in supernatants of cells treated with IDV alone (FIG. 3A; P<0.05, repeated-measures ANOVA). The effect of CQ was not dose-dependent, suggesting that the anti-HIV-1 potency of the CQ/IDV combination might decrease paralleling the increase in the concentration of CQ.

Figure 3:
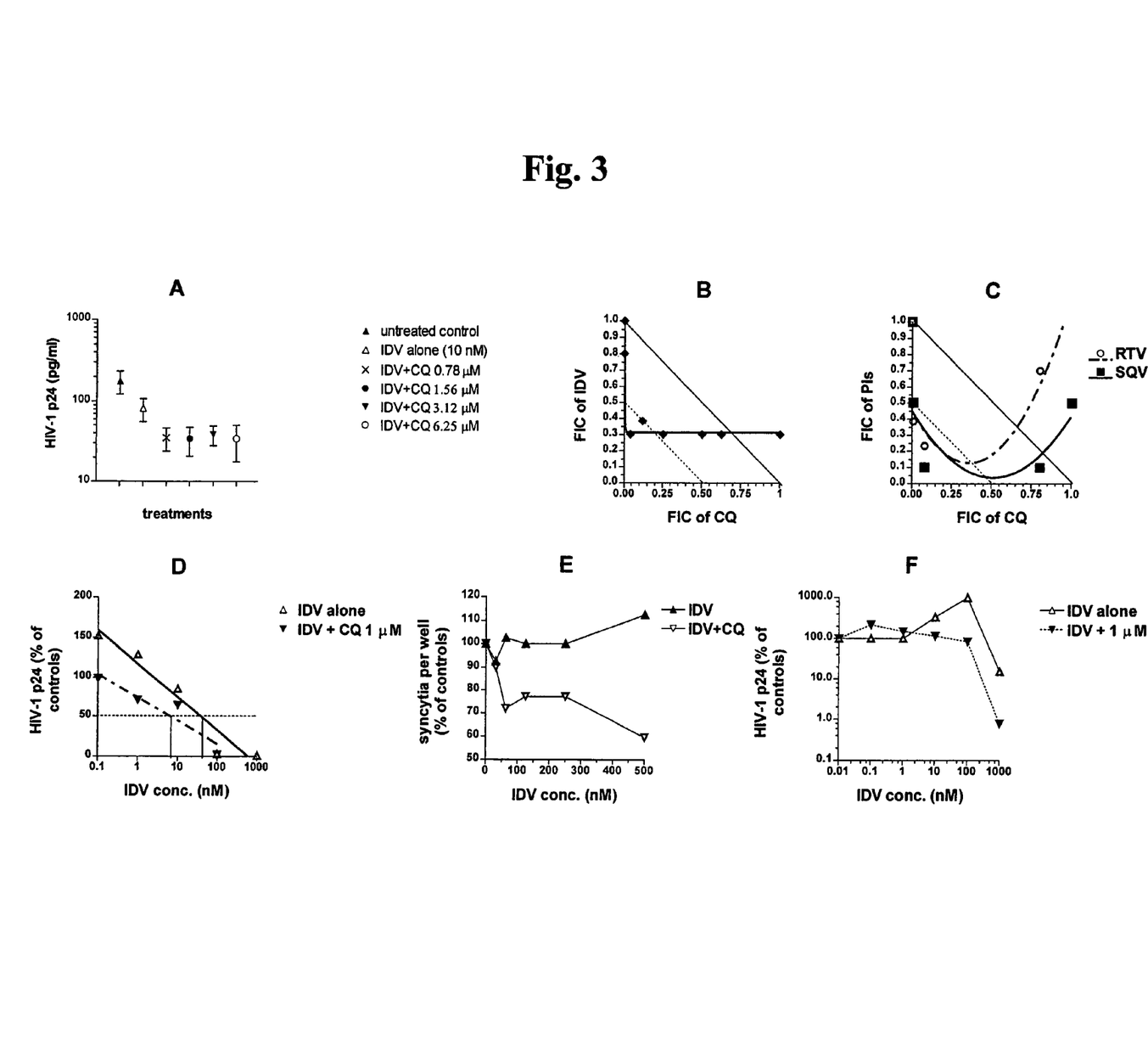
FIG. 3E shows the partial restoration by CQ of the response to IDV in the PAVIA12 multi-drug resistant isolate from HIV-1 Clade B.
FIG. 3F shows the partial restoration by CQ of the response to IDV of an isolate belonging to HIV-1 Clade A. This isolate (UG3) resembles some PI-resistant viruses with a peak in viral replication in the presence of intermediate concentrations of a PI. From this graph, it is evident that CQ induces a shift of the IDV-induced peak of viral replication to the lowest nanomolar concentrations of the PI. The lower amplitude of the peak in the presence of CQ is likely to be attributable to the direct anti-HIV effects of the antimalarial drug.

To better explore this phenomenon, the effects of different CQ/IDV combinations were determined to evaluate whether the effects of the combination were additive, synergistic or sub-synergistic. HIV-1$_{IIIB}$-infected cells were treated with various concentrations of CQ or IDV alone, or in combination. Tests were conducted to evaluate the concentrations of each drug in the different combinations that produced 90% inhibition of HIV-1 replication. For each drug combination, the FIC was determined. Analysis using the isobolograms methods showed that the effect of CQ on the anti-HIV-1 activity of IDV was synergistic at the low FICs of CQ (corresponding to prophylactic antimalarial plasma concentrations, i.e. ≅0.1-1 μM, sub-synergistic or additive at intermediate FICs (≅3.12-6.25 μM), and slightly antagonistic at the highest FICs of CQ (≅≧10 μM, clinically non relevant concentration). Similar effects were obtained with HIV-2 (not shown) and using CQ in combination with RTV or SQV (FIG. 3B). The results show that concentrations of CQ as found during malaria prophylaxis exert a synergistic anti-HIV effect in combination with PIs. The impact of CQ treatment on susceptibility to IDV of primary HIV isolates was then tested. For this purpose, PHA-stimulated peripheral blood mononuclear cells (PBMC) were infected with primary HIV-1 isolates, washed, and incubated with increasing concentrations of IDV (0-1000 nM), in the presence or absence of 1 μM of CQ. Results indicated that the levels of p24 in 5-days old supernatants were lower in cultures treated with IDV+CQ than in cultures treated with matched IDV concentrations without CQ. FIG. 3D shows the typical effect of CQ on an IDV-sensitive isolate belonging to subtype C (VI 829). In this case, CQ lowered the $EC_{50}$ by approximately 1 Log. Moreover, CQ partially restored the response to IDV in a polyresistant HIV-1 isolate (FIG. 3E). We then tested the effects of the IDV/CQ combination on an isolate (UG3) belonging to the "West-African" HIV-1 subtype A. At 5 days after infection by the UG3 isolate, cells incubated with 100 nM IDV presented a typical peak in the p24 levels in supernatants, resembling the increase in infectivity described in PI-resistant virions from subtype B in the presence of similar PI concentrations. Mammano F, Trouplin V, Zennou V, Clavel F. Retracing the evolutionary pathways of human immunodeficiency virus type 1 resistance to protease inhibitors: virus fitness in the absence and in the presence of drug. J Virol. 2000 September;74(18):8524-31. Inhibitory effects were instead visible using IDV at 1 µM. In the presence of CQ, the peak of p24 levels shifted to the lowest nanomolar IDV concentrations (far lower than those reached clinically) and inhibition was restored using IDV starting from 100 nM (FIG. 3F). On the whole, these results are in line with the synergistic effect of CQ on response to IDV. Indeed, they cannot be attributed to a merely additive effect in that the inhibitory effect of CQ alone at a 1 µM concentration is minimal (data not shown).

These differences are unlikely to be attributed to toxic effects exerted by the CQ+IDV combination, as the cell viability values of PBMC treated with 1 µM CQ were essentially identical to those of cells treated with the same IDV concentrations in the absence of CQ (data not shown).

Example II

Figure 4:
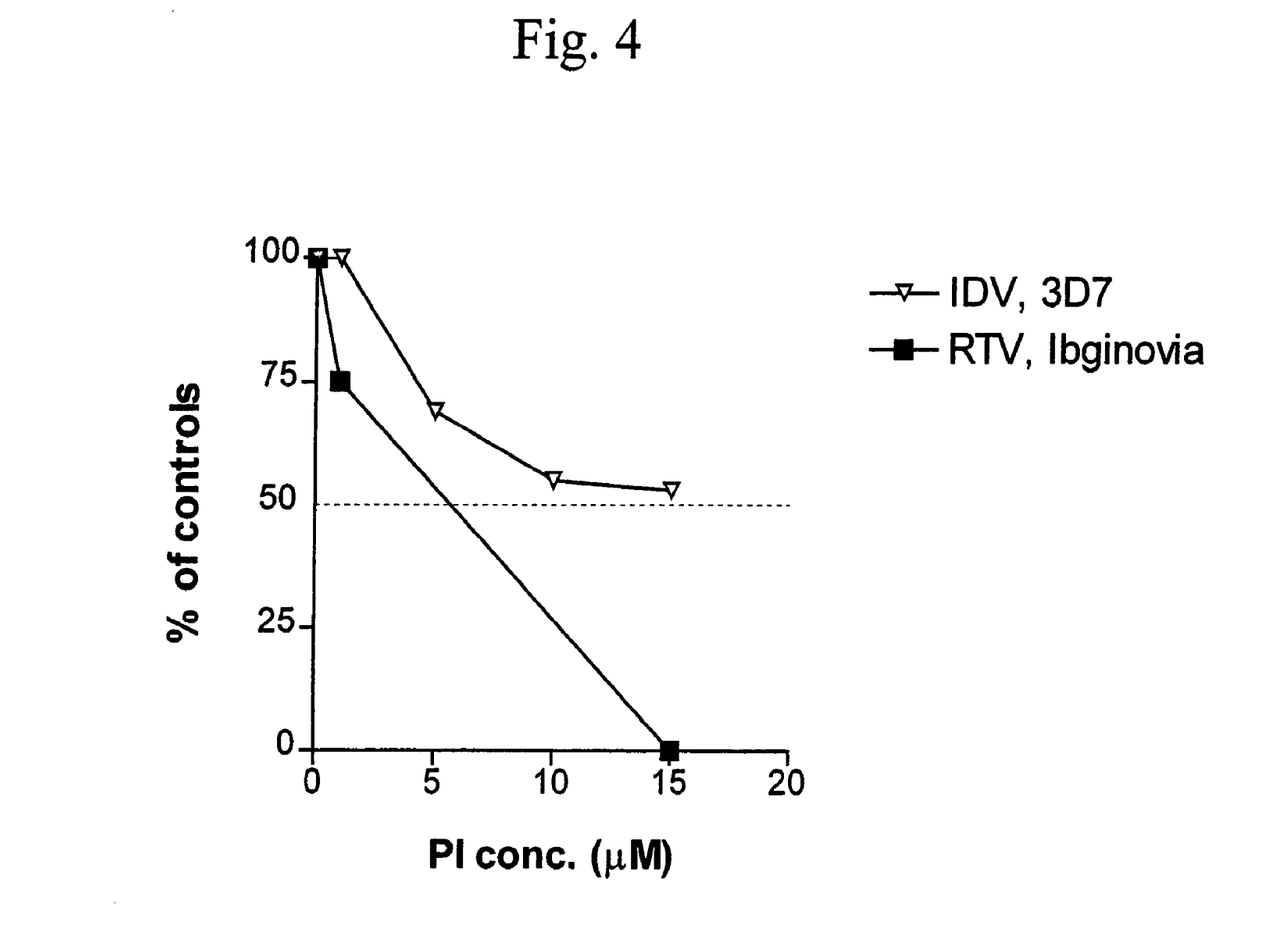
FIG. 4 shows the effects of the HIV protease inhibitors RTV and IDV on a laboratory plasmodium strain (3D7) and on a field isolate (Ibginovia). Results are shown as a percentage of control values.
Figure 5:
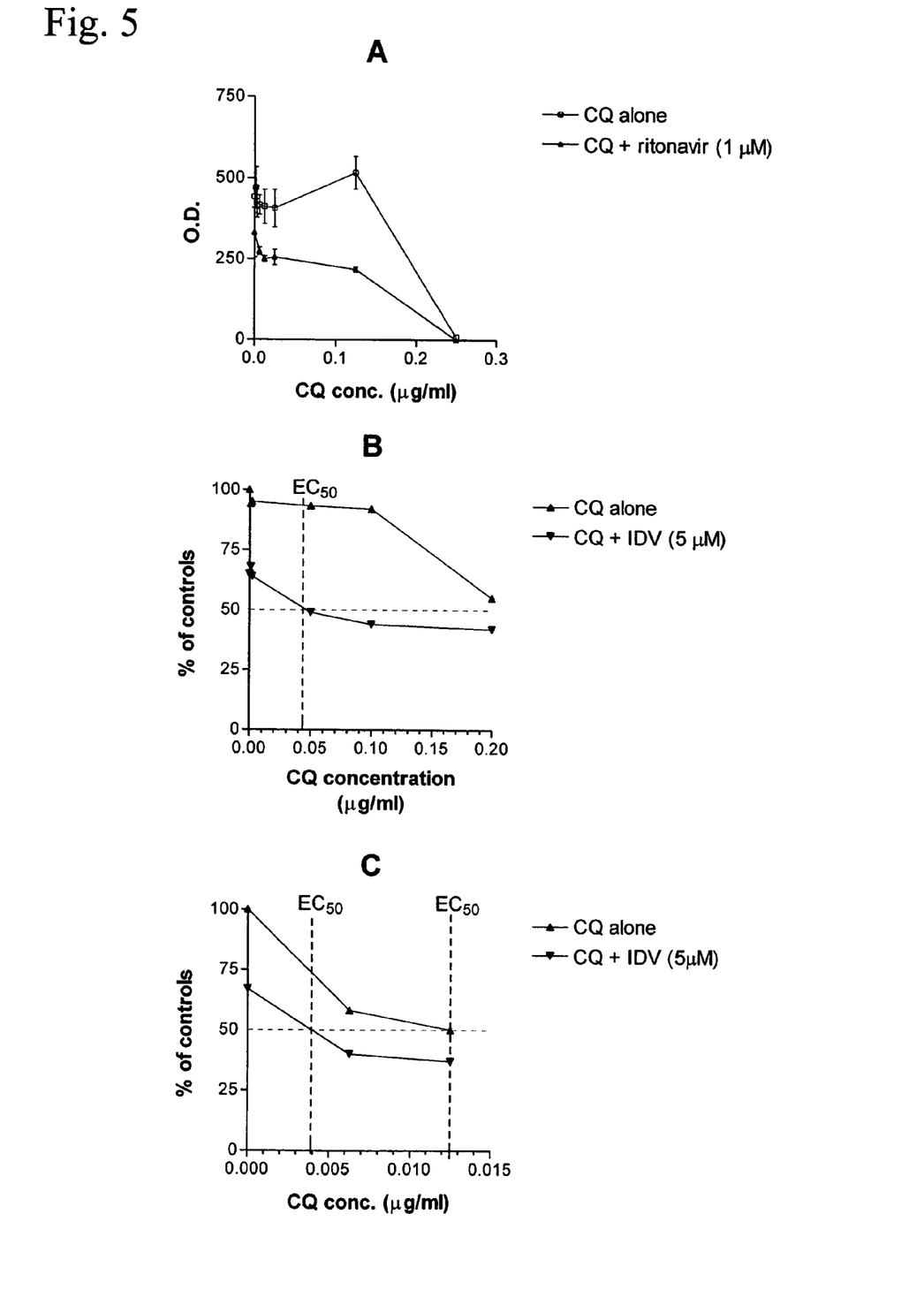
FIG. 5A shows the effects of the HIV-1 protease inhibitor ritonavir in combination with CQ on a CQ-resistant *P. falciparum* field isolate (Ibginovia). In order to illustrate typical results, data are shown as a mean ±S.D. optical density (O.D.) at the end of a reaction mediated by plasmodial lactate dehydrogenase (LDH), as described in the Materials and Methods of the EXAMPLES section. The O.D. values are directly proportional to *P. falciparum* cell viability.
FIG. 5B shows the effects of IDV (5 μM) in combination with CQ on a CQ-resistant *P. falciparum* strain (W2). Results are shown as a percentage of control values.
FIG. 5C shows the effects of IDV (5 μM) on a CQ-sensitive *P. falciparum* strain (3D7). Results are shown as a percentage of control values.

Before performing experiments on the CQ+PIs association, the effects of protease inhibitors when administered alone to *P. falciparum* parasited erythrocytes were evaluated. *P. falciparum*-parasited erythrocytes (starting parasitemia ≅1%) were cultivated for 48 h with concentrations of IDV and RTV lying within the range clinically observable in individuals treated with these PIs. Aliquots of the eryhthrocyte cell suspensions were then collected and assayed for *P. falciparum* LDH activity. Results indicated that RTV and IDV dose-dependently inhibited *P. falciparum* growth. (FIG. 4),

*P. falciparum*-parasited erythrocytes were cultivated for 48 h with decreasing concentrations of CQ in the presence or absence of a PI and then assayed for *P. falciparum* LDH activity as a measure of cell viability. FIGS. 5A and 5B show typical results obtainable with the combination of a PI with CQ. From these data it is evident that RTV and IDV restored the response to CQ in CQ-resistant *P. falciparum*, when these PIs were used at concentrations which per se sub-optimally inhibit *P. falciparum* growth. In a CQ-sensitive *P.falciparum* strain (3D7) the effects of IDV on CQ-response were less dramatic, as shown in FIG. 5C.

In order to determine whether the effects of the CQ+PI combination were only additive or synergistic, the inventor analyzed the response of the W2 (CQ-resistant) and 3D7 (CQ-sensitive) strains to IDV with the method of the sum of FICs. These analyses reported values ≦0.5 (indicating a synergistic effect) on the W2 strain and values >0.5 in the case of the 3D7 strain. As synergism was observed only in the CQ-resistant strain, but not in that CQ-sensitive, it can be concluded that IDV restores sensitivity to chloroquine. The effects on the CQ-resistant strain were thus not merely attributable to the addition of those of IDV to those of CQ.

On the whole, these results indicate that PIs revert CQ-resistance in a verapamil-like manner.

Example III

Figure 6:
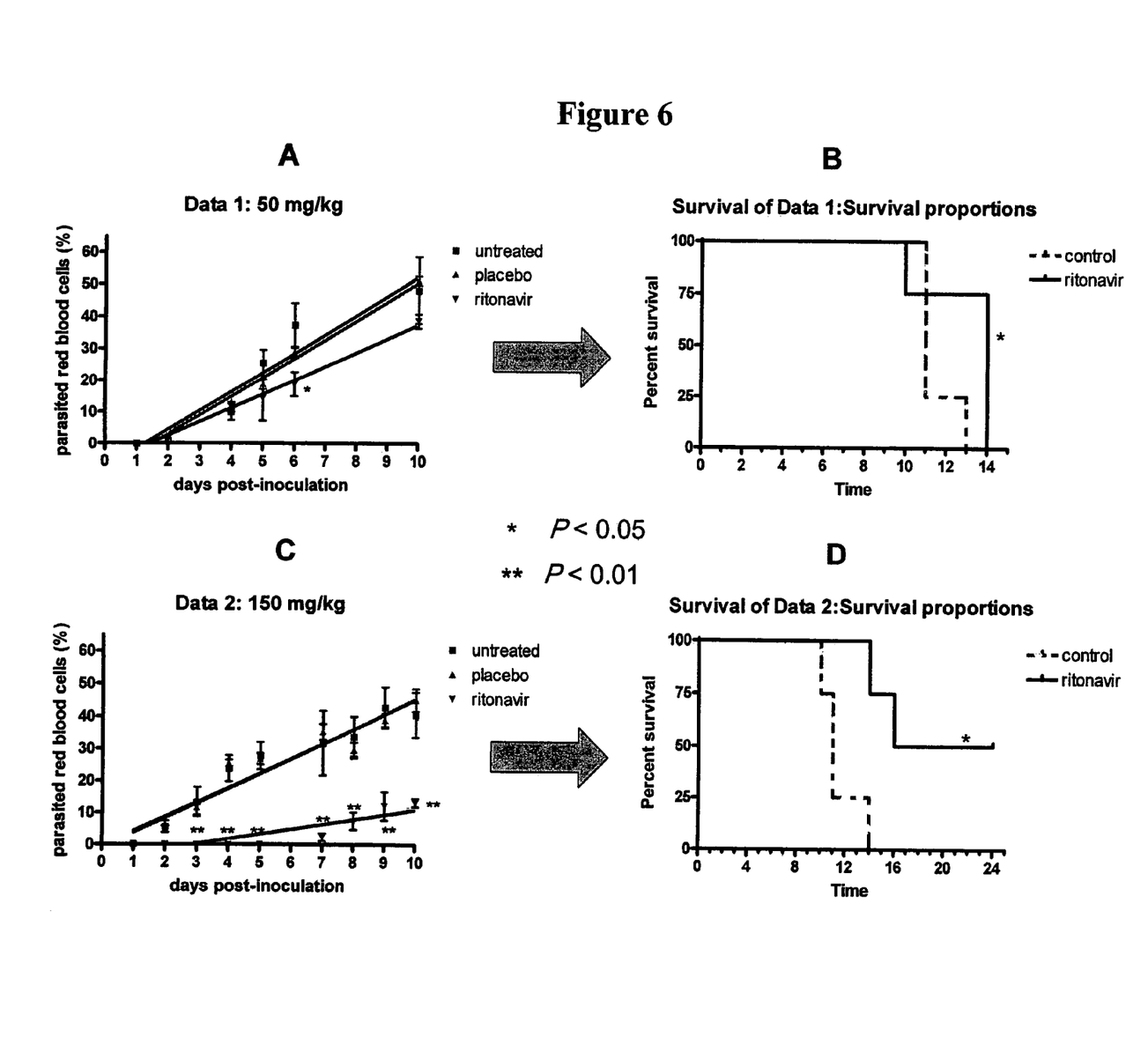
FIG. 6. Antimalarial effects of RTV in mice infected with *Plasmodium berghei*.

To evaluate the effects of a PI in an animal model of malaria, Balb/c mice were inoculated intraperitoneally with *P. berghei* and then divided into three groups: 1) mock-treated with an intragastric inoculation of phosphate-buffer saline (PBS), 2) treated intragastrically with the ritonavir diluent (i.e., a 47% alcoholic solution) in the absence of ritonavir (placebo), and 3) treated intragastrically with 50 or 150 mg/kg. It was determined that ritonavir (treatment 1) dose-dependently retarded parasite multiplication in mice, whereas treatments 2 and 3 had no similar effects (FIGS. 6A and 6C). Of note, ritonavir also increased survival of treated mice in a significant manner, according to the Kaplan-Mayer curves shown in FIGS. 6B and 6D.

Example IV

The antimalarial/PI combinations may be administered using techniques known to those skilled in the art. The antimalarial/PI combinations may be administered in pharmaceutical compositions, including any appropriate excipient, diluent or carrier. The recommended route of administration of the antimalarial/PI combinations may include oral, intramuscular, transdermal, buccal, intravenous or subcutaneous means.

The pharmaceutical compositions may be in the form of tablets, dragees, capsules, pills, solutions, suspensions, emulsions or any other appropriate form for delivery of pharmaceutical compositions. The pharmaceutical compositions in solid form may contain non-aqueous diluents or carriers, including for example fillers, extenders, binding agents, moisturizing agents, disintegrating agents, surface active agents, adsorptive carriers, lubricants or any other appropriate diluent or carrier known to those skilled in the art. Pharmaceutical compositions in liquid form may include diluents or carriers, such as, for example, water, ethyl alcohol, propylene glycol or any other appropriate diluent or carrier known to one skilled in the art. For parenteral administration, solutions and suspensions should be sterile and, if appropriate, blood isotonic.

As used herein, the term "therapeutically effective dose" means a dose of an antimalarial/PI combination that will inhibit replication of HIV and/or *Plasmodium* sp. Therapeutically effective doses can be determined according to standard medical principles under the direction of a physician. The CQ and PI may be provided in any appropriate form for administration, such as for example as a pharmaceutically acceptable salt.

In the prophylactic treatment of malaria, the dosage of PIs used will depend upon the PI chosen for the treatment, and whether the PI is used alone or in combination with other antimalarial drugs. The dosage of the PI administered for treatment of malaria may range from one-half to twice the dosage typically administered for treatment of HIV.

For the treatment of acute malaria, the dosage of the PI administered will also depend upon the PI chosen for treatment, and whether the PI is administered alone or in combination with antimalarial drugs. The dosage of the PI administered for treatment of acute malaria may range from one-half to three times the dosage typically administered for treatment of HIV.

For antimalarial prophylaxis, a combination of CQ and a PI may be administered, with CQ comprising between about 0.8% by weight (in combinations using, for example, amprenavir or saquinavir) to about 15% by weight (in combinations using, for example, vitonavir/lopinavir 1:4 w/w) of the total CQ/PI in the combination. Administration of CQ in an amount less than 2% by weight of the total CQ/PI combination can allow administration of CQ once weekly, with administration of protease inhibitors in a separate formulation at regular intervals during the day, such as every 12 hours or every 8 hours. Administration of the protease inhibitors and the formulations used for administration of the protease inhibitors are in accordance with methods and formulations known to those skilled in the art.

Administration of CQ in an amount greater than 2% to 10% by weight of the total CQ/PI combination (depending on the protease inhibitor used) can be performed by administration of both drugs in a single pharmaceutical formulation, as discussed above. In areas with particularly high levels of CQ resistance, the amount of CQ administered could be increased up to about 33% by weight of the total amount of CQ and PI in the combination. The CQ and PI can also be administered in separate formulations to achieve the desired dosage of CQ and PI in the patient.

For treatment of acute malaria, the amount of CQ in the CQ/PI combination may be increased to about 75% by weight of the total of CQ and PI in the combination. The CQ and PI could be administered in separate formulations to achieve the desired levels in the patient, or the CQ and PI could be combined and administered in a single formulation. When CQ and PI are combined in a single formulation, additional CQ may be administered alone in a separate formulation prior to or at about the time of administration of the first dose of the CQ/PI combination. This additional dose of CQ is administered to reach an appropriate loading of cells with CQ.

The dosage of the PI administered for treatment of HIV may range from one-quarter to the full dosage typically administered for treatment of HIV in the absence of CQ or other antimalarial agents.

In the treatment of HIV infection, CQ and a PI are combined such that CQ comprises from about 0.8% by weight to about 33% by weight of the total weight of CQ/PI in the combination. The CQ/PI may be administered in a single formulation. Alternatively, the CQ and PI may be administered in separate formulations to achieve the desired relative amounts of CQ and PI.

Preferably, the CQ and PI are administered to achieve a blood plasma concentration of CQ between about 0.05 µM and about 1 µM, for the treatment of HIV, and between about 0.005 µM and about 6 µM for the clinical management of malaria. Preferably, the CQ and PI are administered to achieve a blood plasma concentration of the PI of between about 500 nM and about 30 µM, for the clinical management of malaria, and between about 10 nanomolar and about 30 micromolar, for the treatment of HIV. It will be recognized by those skilled in the art that the invention is not limited in this regard, and any appropriate therapeutically effective dose of CQ and PI may be administered.

I claim:

1. A method of treating malaria in humans comprising administering to a patient in need thereof a therapeutically effective amount of a composition comprising:
at least one inhibitor of the HIV protease, or pharmaceutically acceptable salt thereof, selected from the group consisting of indinavir (IDV), ritonavir (RTV), saquinavir (SQV), nelfinavir (NFV), lopinavir (LPV), amprenavir (APV), fosamprenavir, tipranavir, atazanavir, TMC-114, and combinations thereof, in an amount that is therapeutically effective to inhibit the growth of *Plasmodium* sp.

2. The method of claim 1, wherein the therapeutically effective amount of said inhibitor of the HJV protease comprises ritonavir at a dose of from about 1 mg per kg of body weight to about 150 mg per kg of body weight.

* * * * *

SEQUENCE LISTING

```
<160> NUMBER OF SEQ ID NOS: 2

<210> SEQ ID NO 1
<211> LENGTH: 99
<212> TYPE: PRT
<213> ORGANISM: Human
<220> FEATURE:
<221> NAME/KEY: misc_feature
<222> LOCATION: (1)..(99)
<223> OTHER INFORMATION: LOCUS        CAC86554
<300> PUBLICATION INFORMATION:
<308> DATABASE ACCESSION NUMBER: NCBI/AJ318510.1
<309> DATABASE ENTRY DATE: 2002-01-04
<313> RELEVANT RESIDUES: (1)..(99)

<400> SEQUENCE: 1

Pro Gln Ile Thr Leu Trp Gln Arg Pro Ile Val Thr Ile Lys Ile Gly
1               5                   10                  15

Gly Gln Leu Lys Glu Ala Leu Leu Asp Thr Gly Ala Asp Asp Thr Val
            20                  25                  30

Leu Gln Glu Met Asn Leu Pro Gly Arg Trp Lys Pro Lys Met Ile Val
        35                  40                  45

Gly Ile Gly Gly Phe Val Lys Val Arg Gln Tyr Asp Gln Val Pro Ile
    50                  55                  60

Glu Ile Cys Gly His Lys Val Ile Gly Thr Val Leu Ile Gly Pro Thr
65                  70                  75                  80

Pro Val Asn Ile Ile Gly Arg Asn Leu Leu Thr Gln Leu Gly Cys Thr
                85                  90                  95

Leu Asn Phe

<210> SEQ ID NO 2
<211> LENGTH: 453
<212> TYPE: PRT
<213> ORGANISM: Plasmodium falciparum
<220> FEATURE:
<221> NAME/KEY: PEPTIDE
<222> LOCATION: (1)..(453)
<300> PUBLICATION INFORMATION:
```

<308> DATABASE ACCESSION NUMBER: NCBI/P46925
<309> DATABASE ENTRY DATE: 1995-11-01
<313> RELEVANT RESIDUES: (1)..(453)

<400> SEQUENCE: 2

```
Met Asp Ile Thr Val Arg Glu His Asp Phe Lys His Gly Phe Ile Lys
1               5                   10                  15

Ser Asn Ser Thr Phe Asp Gly Leu Asn Ile Asp Asn Ser Lys Asn Lys
            20                  25                  30

Lys Lys Ile Gln Lys Gly Phe Gln Ile Leu Tyr Val Leu Leu Phe Cys
        35                  40                  45

Ser Val Met Cys Gly Leu Phe Tyr Tyr Val Tyr Glu Asn Val Trp Leu
    50                  55                  60

Gln Arg Asp Asn Glu Met Asn Glu Ile Leu Lys Asn Ser Glu His Leu
65                  70                  75                  80

Thr Ile Gly Phe Lys Val Glu Asn Ala His Asp Arg Ile Leu Lys Thr
                85                  90                  95

Ile Lys Thr His Lys Leu Lys Asn Tyr Ile Lys Glu Ser Val Asn Phe
            100                 105                 110

Leu Asn Ser Gly Leu Thr Lys Thr Asn Tyr Leu Gly Ser Ser Asn Asp
        115                 120                 125

Asn Ile Glu Leu Val Asp Phe Gln Asn Ile Met Phe Tyr Gly Asp Ala
130                 135                 140

Glu Val Gly Asp Asn Gln Gln Pro Phe Thr Phe Ile Leu Asp Thr Gly
145                 150                 155                 160

Ser Ala Asn Leu Trp Val Pro Ser Val Lys Cys Thr Thr Ala Gly Cys
                165                 170                 175

Leu Thr Lys His Leu Tyr Asp Ser Ser Lys Ser Arg Thr Tyr Glu Lys
            180                 185                 190

Asp Gly Thr Lys Val Glu Met Asn Tyr Val Ser Gly Thr Val Ser Gly
        195                 200                 205

Phe Phe Ser Lys Asp Leu Val Thr Val Gly Asn Leu Ser Leu Pro Tyr
210                 215                 220

Lys Phe Ile Glu Val Ile Asp Thr Asn Gly Phe Glu Pro Thr Tyr Thr
225                 230                 235                 240

Ala Ser Thr Phe Asp Gly Ile Leu Gly Leu Gly Trp Lys Asp Leu Ser
                245                 250                 255

Ile Gly Ser Val Asp Pro Ile Val Val Glu Leu Lys Asn Gln Asn Lys
            260                 265                 270

Ile Glu Asn Ala Leu Phe Thr Phe Tyr Leu Pro Val His Asp Lys His
        275                 280                 285

Thr Gly Phe Leu Thr Ile Gly Gly Ile Glu Glu Arg Phe Tyr Glu Gly
290                 295                 300

Pro Leu Thr Tyr Glu Lys Leu Asn His Asp Leu Tyr Trp Gln Ile Thr
305                 310                 315                 320

Leu Asp Ala His Val Gly Asn Ile Met Leu Glu Lys Ala Asn Cys Ile
                325                 330                 335

Val Asp Ser Gly Thr Ser Ala Ile Thr Val Pro Thr Asp Phe Leu Asn
            340                 345                 350

Lys Met Leu Gln Asn Leu Asp Val Ile Lys Val Pro Phe Leu Pro Phe
        355                 360                 365

Tyr Val Thr Leu Cys Asn Asn Ser Lys Leu Pro Thr Phe Glu Phe Thr
370                 375                 380

Ser Glu Asn Gly Lys Tyr Thr Leu Glu Pro Glu Tyr Tyr Leu Gln His
```

-continued

```
385                 390                 395                 400
Ile Glu Asp Val Gly Pro Gly Leu Cys Met Leu Asn Ile Ile Gly Leu
            405                 410                 415

Asp Phe Pro Val Pro Thr Phe Ile Leu Gly Asp Pro Phe Met Arg Lys
            420                 425                 430

Tyr Phe Thr Val Phe Asp Tyr Asn His Ser Val Gly Ile Ala Leu
            435                 440                 445

Ala Lys Lys Asn Leu
            450
```